United States Patent
Kurosawa et al.

(10) Patent No.: US 12,285,158 B2
(45) Date of Patent: Apr. 29, 2025

(54) INTRAORAL MEASUREMENT DEVICE

(71) Applicant: Konica Minolta, Inc., Tokyo (JP)

(72) Inventors: Takashi Kurosawa, Hachioji (JP); Atsushi Nagaoka, Okazaki (JP); Yoshihiro Inagaki, Hachioji (JP); Mohdmakhtar Nurnabila, Hachioji (JP)

(73) Assignee: Konica Minolta, Inc., Tokyo (JP)

( * ) Notice: Subject to any disclaimer, the term of this patent is extended or adjusted under 35 U.S.C. 154(b) by 286 days.

(21) Appl. No.: 17/731,352

(22) Filed: Apr. 28, 2022

(65) Prior Publication Data

US 2022/0361742 A1 Nov. 17, 2022

(30) Foreign Application Priority Data

May 11, 2021 (JP) ................................. 2021-080104

(51) Int. Cl.
*A61B 1/24* (2006.01)
*A61B 5/00* (2006.01)

(52) U.S. Cl.
CPC .............. *A61B 1/24* (2013.01); *A61B 5/4547* (2013.01); *A61B 5/4552* (2013.01)

(58) Field of Classification Search
CPC ....... A61B 1/24; A61B 5/4547; A61B 5/4552; A61B 1/00096; A61B 1/00101; A61B 1/00137; A61B 1/0669; A61B 1/128; A61B 1/253; A61B 5/0088; A61C 9/0053
See application file for complete search history.

(56) References Cited

U.S. PATENT DOCUMENTS

| | | | | |
|---|---|---|---|---|
| 1,934,110 A | * | 11/1933 | Wilson | A61B 1/253 433/32 |
| 4,757,381 A | * | 7/1988 | Cooper | A61B 1/00142 433/116 |
| 4,867,136 A | * | 9/1989 | Suzuki | A61B 1/00165 600/109 |
| 5,251,025 A | * | 10/1993 | Cooper | A61B 1/00091 600/160 |
| 5,605,532 A | * | 2/1997 | Schermerhorn | A61B 1/127 600/176 |
| 5,700,236 A | * | 12/1997 | Sauer | A61B 1/00096 600/175 |

(Continued)

FOREIGN PATENT DOCUMENTS

JP 2011087733 A * 5/2011 .............. A61B 1/24

*Primary Examiner* — Mohamed K Amara
(74) *Attorney, Agent, or Firm* — RANKIN, HILL & CLARK LLP

(57) ABSTRACT

An intraoral measurement device includes: a device main body that holds a base end side of a prism by a housing, the housing accommodating an illumination member and an imaging member, a cover member that is attached to the device main body in a state of covering, with a space part interposed in between, a distal end side of the prism arranged to face a measurement target, in which a part arranged to face the measurement target is formed by a light transmission window; and a heat transfer member that extends from the device main body along a non-optical surface of the prism, and transfers heat of the device main body to the light transmission window through abutment of a protruding end provided to protrude from the prism against the light transmission window of the cover member.

14 Claims, 7 Drawing Sheets

(56) References Cited

U.S. PATENT DOCUMENTS

| | | | | |
|---|---|---|---|---|
| 5,894,369 A * | 4/1999 | Akiba | | G02B 23/2423 600/110 |
| 6,364,660 B1 * | 4/2002 | Durbin | | G06T 17/00 433/29 |
| 6,633,789 B1 * | 10/2003 | Nikolskiy | | B33Y 50/00 700/118 |
| 6,979,196 B2 * | 12/2005 | Nikolskiy | | A61C 19/05 433/214 |
| 7,255,558 B2 * | 8/2007 | Babayoff | | A61C 17/022 433/29 |
| 7,946,846 B2 * | 5/2011 | Babayoff | | A61C 9/006 433/29 |
| 9,491,863 B2 * | 11/2016 | Boltanski | | G02B 27/123 |
| 9,844,426 B2 * | 12/2017 | Atiya | | A61B 1/00009 |
| 10,390,913 B2 * | 8/2019 | Sabina | | G06T 19/00 |
| 10,456,043 B2 * | 10/2019 | Atiya | | A61C 7/002 |
| 10,492,893 B2 * | 12/2019 | Van Der Poel | | A61B 1/253 |
| 10,507,087 B2 * | 12/2019 | Elbaz | | A61B 1/00045 |
| 10,517,482 B2 * | 12/2019 | Sato | | A61C 7/002 |
| 10,849,723 B1 * | 12/2020 | Yancey | | A61C 7/002 |
| 10,952,816 B2 * | 3/2021 | Kopelman | | A61C 1/082 |
| 10,959,609 B1 * | 3/2021 | Swift | | A61B 1/0684 |
| 11,510,561 B2 * | 11/2022 | Rephaeli | | A61B 1/0638 |
| 11,583,166 B2 * | 2/2023 | Tanaka | | A61B 1/00096 |
| 11,653,825 B2 * | 5/2023 | Ichihara | | A61B 1/00174 600/160 |
| 12,011,337 B2 * | 6/2024 | Fridman | | A61B 5/0086 |
| 2002/0135694 A1 * | 9/2002 | Williams | | A61B 1/00177 348/E5.025 |
| 2003/0107652 A1 * | 6/2003 | Williams | | A61B 1/042 348/E5.025 |
| 2005/0283065 A1 * | 12/2005 | Babayoff | | A61B 5/0088 600/407 |
| 2007/0073108 A1 * | 3/2007 | Takahashi | | A61B 1/127 600/176 |
| 2007/0149856 A1 * | 6/2007 | Segawa | | A61B 1/127 600/109 |
| 2008/0160477 A1 * | 7/2008 | Stookey | | A61B 1/015 433/29 |
| 2009/0017416 A1 * | 1/2009 | Nguyen | | A61B 1/00105 433/30 |
| 2011/0301414 A1 * | 12/2011 | Hotto | | A61B 1/00082 600/114 |
| 2012/0034573 A1 * | 2/2012 | Erdmann | | A61B 1/0008 433/29 |
| 2013/0197311 A1 * | 8/2013 | Sherwin | | A61B 1/00101 600/177 |
| 2013/0303853 A1 * | 11/2013 | Takahashi | | G02B 23/2476 600/134 |
| 2013/0310644 A1 * | 11/2013 | Ichimura | | A61B 1/051 600/109 |
| 2014/0200406 A1 * | 7/2014 | Bennett | | A61B 1/127 600/109 |
| 2015/0018613 A1 | 1/2015 | Hollenbeck et al. | | |
| 2015/0238072 A1 * | 8/2015 | Makmel | | A61B 1/127 219/221 |
| 2015/0351879 A1 * | 12/2015 | Boltanski | | G02B 7/08 433/29 |
| 2017/0188802 A1 * | 7/2017 | Lawrence | | A61B 1/0607 |
| 2019/0029784 A1 * | 1/2019 | Moalem | | A61C 13/082 |
| 2019/0388193 A1 * | 12/2019 | Saphier | | H04N 9/3161 |
| 2020/0163533 A1 * | 5/2020 | Kim | | A61B 1/253 |
| 2020/0315434 A1 * | 10/2020 | Kopelman | | A61B 1/00103 |
| 2020/0404243 A1 * | 12/2020 | Saphier | | H04N 23/90 |
| 2021/0030503 A1 * | 2/2021 | Shalev | | A61C 9/0053 |
| 2021/0393136 A1 * | 12/2021 | Inagaki | | A61C 19/04 |
| 2022/0000591 A1 * | 1/2022 | Iijima | | A61B 5/682 |
| 2022/0015618 A1 * | 1/2022 | Makmel | | A61C 1/16 |
| 2022/0361742 A1 * | 11/2022 | Kurosawa | | A61B 5/4552 |
| 2023/0218149 A1 * | 7/2023 | Hansen | | A61B 1/253 361/600 |

* cited by examiner

INTRAORAL MEASUREMENT DEVICE

The entire disclosure of Japanese patent Application No. 2021-080104, filed on May 11, 2021, is incorporated herein by reference in its entirety.

BACKGROUND

Technological Field

The present invention relates to an intraoral measurement device.

Description of the Related Art

There is an intraoral measurement device as a technique for measuring an intraoral shape of teeth and gums. As a technique related to such a device, there is a technique disclosed in US 2015/0018613 A. US 2015/0018613 A describes a configuration in which a cover-shaped tip on which a mirror is installed is attached to a tube that is a part of a main body, and the tip is reused by removing and sterilizing the tip at the end of treatment. Further, a configuration is described in which, in order to inhibit condensation on a front window provided at a distal end of the tube and the mirror provided on the tip, a heat conductive sheet is provided at a distal end (tube) of a main body of a scanner, and the heat conductive sheet extends from a back side of the mirror to a region physically in contact with the tube. As a result, heat generated by heating of the tube is transmitted to the front window and the mirror via the heat conductive sheet to raise a temperature of the front window and the mirror, so that condensation of moisture can be inhibited.

As another mode of the intraoral measurement device, there is a configuration in which a distal end part of a main body is formed by a prism, and the distal end part is removably covered with a cover having a light transmission window. In such a configuration, since measurement light enters and exits from the prism via the light transmission window provided in the cover, a heat conductive sheet is unable to be in close contact with the entire surface of the light transmission window.

Moreover, in order to heat the light transmission window provided on the cover side in such a configuration, a distal end of an electrothermal sheet provided on the main body side having a heat source part needs to protrude outward from the prism at a position facing the light transmission window, and a protruding end of the electrothermal sheet needs to abut with the light transmission window in a state where the cover is attached to the main body.

However, since a prism surface arranged facing the light transmission window is a total reflection surface, and an air layer is required between the prism and the light transmission window, some joining backlash occurs at a position of the prism with respect to the cover. As a result, it has not been easy for the protruding end of the electrothermal sheet to abut with the light transmission window, and it has not been possible to reliably inhibit condensation on the light transmission window.

SUMMARY

Therefore, an object of the present invention is to provide an intraoral measurement device capable of reliably inhibiting condensation on a light transmission window in a configuration in which a prism is covered with a cover having the light transmission window via a space part.

To achieve the abovementioned object, according to an aspect of the present invention, an intraoral measurement device reflecting one aspect of the present invention comprises: a device main body that holds a base end side of a prism by a housing, the housing accommodating an illumination member and an imaging member, a cover member that is attached to the device main body in a state of covering, with a space part interposed in between, a distal end side of the prism arranged to face a measurement target, in which a part arranged to face the measurement target is formed by a light transmission window; and a heat transfer member that extends from the device main body along a non-optical surface of the prism, and transfers heat of the device main body to the light transmission window through abutment of a protruding end provided to protrude from the prism against the light transmission window of the cover member, wherein on a non-optical surface of the prism, a positioning member protruding from the non-optical surface in a direction opposite to the protruding end of the heat transfer member is provided, and the positioning member presses the prism and the protruding end of the heat transfer member toward the light transmission window, by being pressed toward the protruding end by an inner wall of the cover member attached to the device main body.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Figure 1:
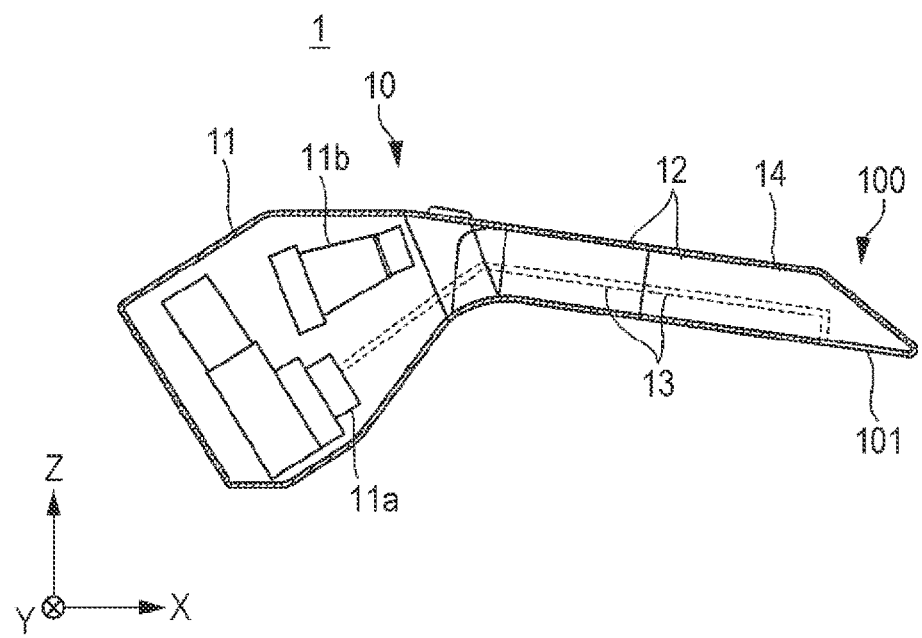
FIG. 1 is an overall configuration view (part 1) for explaining a configuration of an intraoral measurement device according to a first embodiment.

Hereinafter, one or more embodiments of the present invention will be described with reference to the drawings. However, the scope of the invention is not limited to the disclosed embodiments. Note that, in each embodiment described below, the same components are denoted by the same reference numerals, and redundant description will be omitted.

First Embodiment

Figure 2:
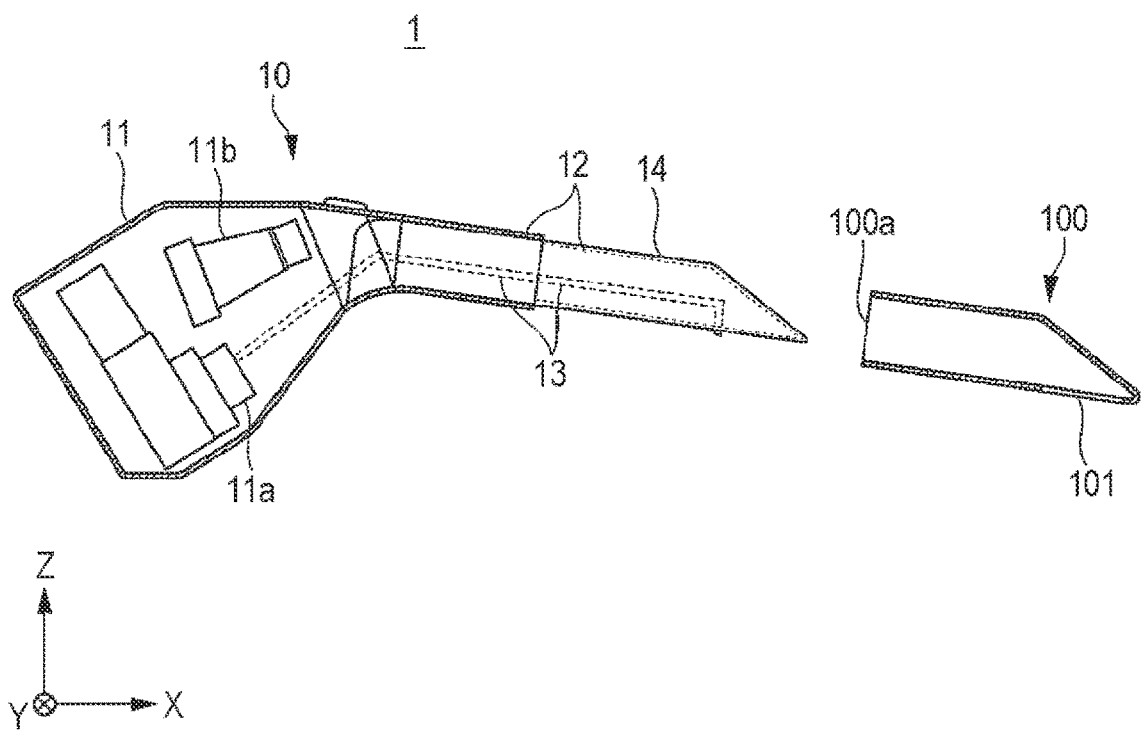
FIG. 2 is an overall configuration view (part 2) for explaining the configuration of the intraoral measurement device according to the first embodiment.

FIGS. 1 and 2 are overall configuration views (part 1) and (part 2) for explaining a configuration of an intraoral measurement device 1 according to a first embodiment. The intraoral measurement device 1 illustrated in these figures is, for example, for capturing a 3D image in an oral cavity, and includes a device main body 10 and a cover member 100 removable from the device main body 10. FIG. 1 is an overall configuration view of a state where the cover member 100 is attached to the device main body 10, and FIG. 2 is an overall configuration view of a state where the cover member 100 is removed from the device main body 10. Hereinafter, configurations of the device main body 10 and the cover member 100 will be sequentially described.

<Device Main Body 10>

The device main body 10 includes a housing 11 in which an optical component is accommodated, a prism 12 provided with a distal end side protruding from the housing 11, a heat transfer member 13 provided on a side wall of the prism 12, and a positioning member 14. Further, the device main body 10 including these members also includes a heat source. Hereinafter, each element constituting the device main body 10 is described.

[Housing 11]

The housing 11 accommodates the optical component, and holds a base end side of the prism 12. The optical components accommodated in the housing 11 are an illumination member 11a and an imaging member 11b. The housing 11 accommodates these optical components such that measuring light emitted from the illumination member 11a is made incident on the prism 12, and measurement light that is emitted from the prism 12, reflected by a measurement target (not illustrated), and incident on the prism 12 again is incident on the imaging member 11b. Among them, the illumination member 11a includes a light source such as a light emitting diode (LED), for example. This light source is an example of a heat source of the heat transfer member 13 described below. Note that the heat source of the heat transfer member 13 is not limited to the light source provided in the illumination member 11a, and may be another member constituting the device main body 10, for example, the housing 11 or another member whose description is omitted here.

[Prism 12]

The prism 12 has an elongated shape extending from the housing 11, and a distal end side of the elongated shape extending from the housing 11 is inserted into the oral cavity. To the distal end side, the cover member 100 is attached. In the prism 12, an end part held by the housing 11 is a base end side, and the illumination member 11a and the imaging member 11b are arranged on the base end side.

Figure 3:
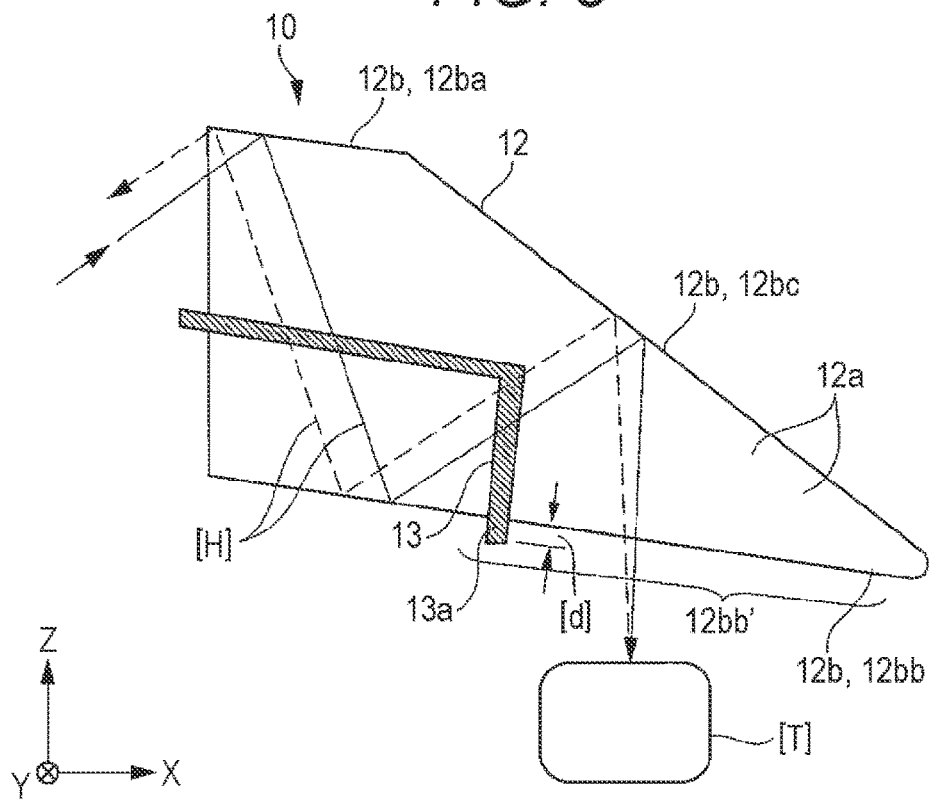
FIG. 3 is an enlarged view (part 1) of a main part for explaining the configuration of the intraoral measurement device according to the first embodiment.

FIG. 3 is an enlarged view (part 1) of a main part for explaining a configuration of the intraoral measurement device 1 according to the first embodiment, which is an enlarged view of the distal end side of the prism 12 and is a view illustrating an optical path of measurement light [H]. Referring to FIGS. 3, 1, and 2, the prism 12 internally reflects the measurement light [H] supplied from the illumination member 11a for a plurality of times to guide the measurement light [H] to the distal end side, and irradiates a measurement target [T] with the measurement light [H]. The measurement target M is, for example, teeth or gums in an oral cavity. Further, the prism 12 internally reflects the measurement light [H] reflected by the measurement target M for a plurality of times to guide the measurement light [H] to the imaging member 11b.

Here, as an example, the prism 12 has a non-optical surface 12a facing the front in the figure and another non-optical surface 12a substantially parallel to this, and is a rectangular column having these non-optical surfaces 12a as a bottom surface. A side peripheral wall of the rectangular column is arranged perpendicular to an xz plane and parallel to a y direction. In such a prism 12, a plurality of side peripheral walls arranged perpendicular to the xz plane serve as optical surfaces 12b. These optical surfaces 12b are surfaces including all planes. Among them, an optical surface on the base end side of the prism 12, which is not illustrated in FIG. 3, is a light transmitting surface, and other optical surfaces 12b are light reflecting surfaces that totally reflect the measurement light [H].

Further, the optical surfaces 12b of the prism 12 are, for example, a first surface 12ba, a second surface 12bb, and a third surface 12bc in the order of arrival of the measurement light [H] emitted from the illumination member 11a, for example, except for the optical surface on the base end side of the prism 12, which is not illustrated in FIG. 3. After being totally reflected by the third surface 12bc, the measurement light [H] is emitted again to the second surface 12bb, passes through the second surface 12bb, and is emitted to the measurement target [T]. Then, in the second surface 12bb, in particular, a region arranged to face the measurement target [T] and through which the measurement light [H] is transmitted is referred to as an objective surface 12bb'.

[Heat Transfer Member 13]

Referring to FIGS. 1 to 3, the heat transfer member 13 is a thin plate-shaped long member made with a material having a good thermal conductivity, such as silver, copper, gold, aluminum, nickel, or platinum. Such a heat transfer member 13 is drawn out from a light source part serving as a heat source in the illumination member 11a, extends along the non-optical surface 12a of the prism 12, and is arranged to protrude from the prism 12 on a side of the objective surface 12bb'.

In the heat transfer member 13, a length of a protruding end 13a protruding from the prism 12, that is, a protruding length [d] (see FIG. 3) is made slightly larger than a distance between the optical surface 12b (particularly, the second surface 12bb) and an inner wall of the cover member 100 when the cover member 100 is attached to the prism 12.

Such a heat transfer member 13 may be fixed to the device main body 10 including the prism 12 by, for example, adhesion. Further, the heat transfer member 13 may be provided individually along the two non-optical surfaces 12a of the prism 12, or may be provided exclusively on one of the non-optical surfaces 12a.

[Positioning Member 14]

Figure 4:
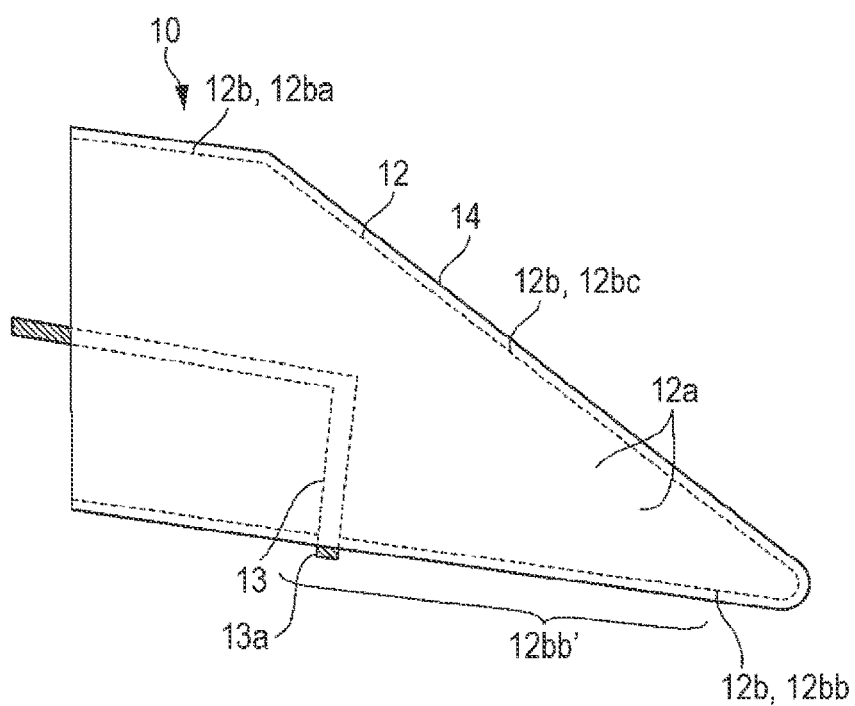
FIG. 4 is an enlarged view (part 2) of a main part for explaining the configuration of the intraoral measurement device according to the first embodiment.

FIG. 4 is an enlarged view (part 2) of a main part for explaining the configuration of the intraoral measurement device according to the first embodiment, which is an enlarged view of the distal end side of the prism 12. As illustrated in this figure, the positioning member 14 has, for example, a sheet shape covering the non-optical surface 12a of the prism 12, and is arranged to overlap with the heat transfer member 13. FIG. 4 illustrates a configuration in which the heat transfer member 13 is sandwiched between the non-optical surface 12a of the prism 12 and the positioning member 14, but the positioning member 14 may be sandwiched between the non-optical surface 12a of the prism 12 and the heat transfer member 13.

Further, the positioning member 14 has a shape protruding outward from the prism 12 on the first surface 12ba side of the optical surface 12b, that is, on a side opposite to a side where the heat transfer member 13 protrudes. Moreover, the positioning member 14 may protrude outward from the prism 12 also on the second surface 12bb side including the objective surface 12bb', that is, the side where the heat transfer member 13 protrudes. Furthermore, as illustrated in the figure, the positioning member 14 may also protrude from the prism 12 on the third surface 12bc side.

A length by which the positioning member 14 protrudes from the prism 12 is a range in which insertion of the prism 12 bonded with the positioning member 14 into the cover member 100 described below is not hindered. In particular, on the second surface 12bb side, the length needs to be shorter than the protruding end 13a of the heat transfer member 13. As a result, abutment of the protruding end 13a of the heat transfer member 13 against the cover member 100 is not hindered by the positioning member 14.

In addition, a thickness of the positioning member 14 is made to be in a range in which insertion of the prism 12 bonded with the positioning member 14 into the cover member 100 described below is not hindered. Furthermore, even when the heat transfer member 13 is arranged exclusively on one of the two non-optical surfaces 12a of the prism 12, the positioning member 14 is preferably arranged on the non-optical surfaces 12a on both sides. This enables to stably maintain the position of the prism 12 inserted into the cover member 100.

Such a positioning member 14 is for pressing the protruding end 13a of the heat transfer member 13 toward the cover member 100 following the positioning member 14, by a peripheral edge on a side opposite to the protruding end 13a of the heat transfer member 13 being pressed toward the protruding end 13a by the inner wall of the cover member 100 described below. A material of such a positioning member 14 is not limited, but may include, for example, a resin material or a metal material, and the positioning member 14 itself may be a heat transfer material.

<Cover Member 100>

Figure 5:
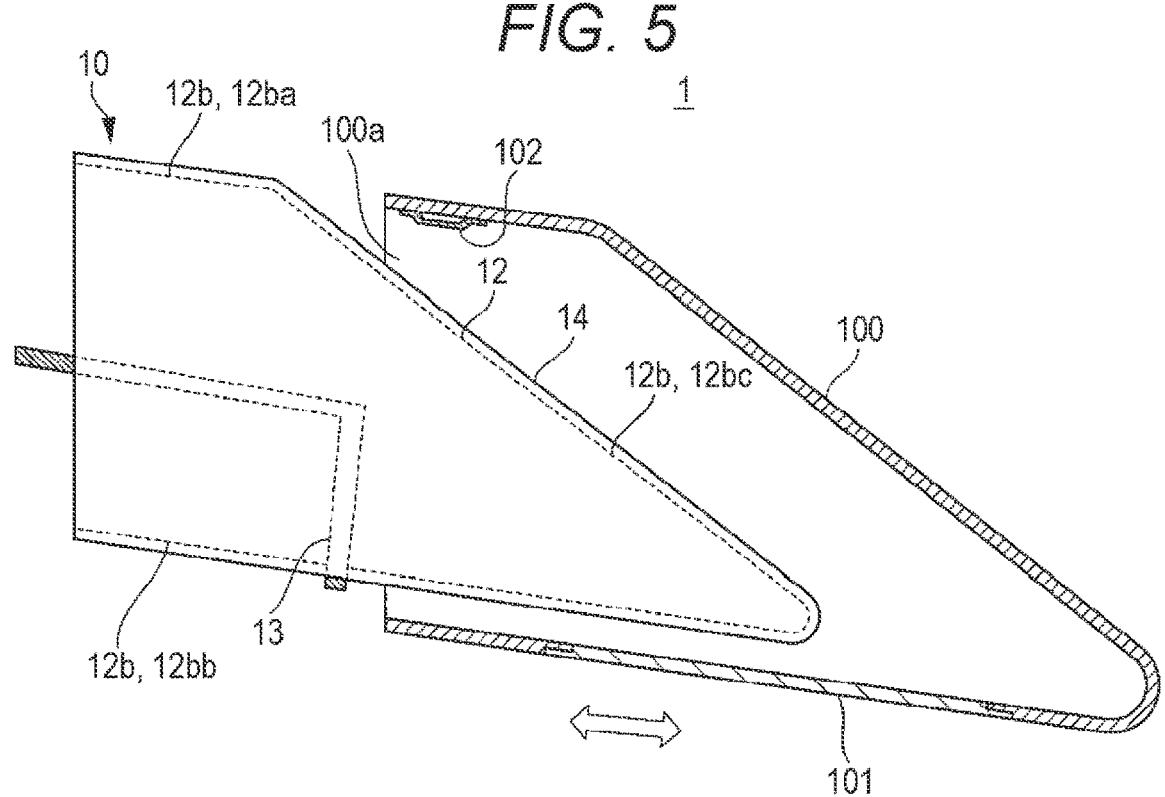
FIG. 5 is an enlarged view (part 3) of a main part for explaining the configuration of the intraoral measurement device according to the first embodiment.
Figure 6:
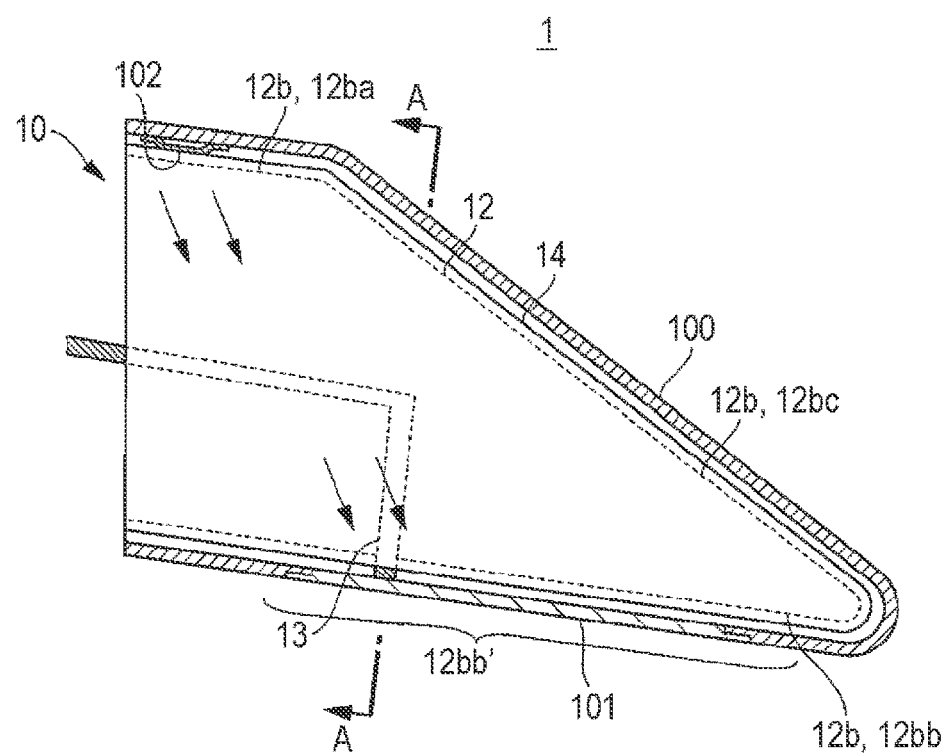
FIG. 6 is an enlarged view (part 4) of a main part for explaining the configuration of the intraoral measurement device according to the first embodiment.

FIGS. 5 and 6 are enlarged views (part 3) and (part 4) of a main part for explaining the configuration of the intraoral measurement device 1 according to the first embodiment, which are enlarged views of the prism 12 and the cover member 100 covering the prism 12. As illustrated in FIGS. 5 and 6 and FIGS. 1 and 2 above, the cover member 100 is a member that covers the distal end side of the prism 12 provided in the device main body 10 so as to protrude from the housing 11, and is removably attached to the device main body 10.

The cover member 100 has a tubular shape following an outer shape of the prism 12, and has one end part closed and another end part serving as an insertion port 100a of the prism 12. Such a cover member 100 forms a space part between with the prism 12, by attaching the cover member 100 to the device main body 10 along the outer shape of the prism 12. This space part serves as an air layer. Further, in this state, the prism 12 is sealed inside the housing 11 and the cover member 100 of the device main body 10. Such a cover member 100 includes a light transmission window 101 and an elastic member 102.

[Light Transmission Window 101]

The light transmission window 101 constitutes a part of a wall part of the cover member 100, and is arranged to face the objective surface 12bb' of the prism 12 in a state where the cover member 100 is attached to the device main body 10. Such a light transmission window 101 is made by glass or a resin material.

[Elastic Member 102]

The elastic member 102 is provided at a position and with a size to press the positioning member 14 from the first surface 12ba side toward the second surface 12bb of the prism 12, in a state where the cover member 100 is attached to the device main body 10. Note that the second surface 12bb of the prism 12 is a surface in a direction in which the heat transfer member 13 protrudes from the prism 12, and is a surface facing the light transmission window 101.

Such an elastic member 102 is provided at a position facing a peripheral edge of the positioning member 14 on an inner wall of the cover member 100 facing the first surface 12ba of the prism 12, in a state where the cover member 100 is attached to the device main body 10, for example. Such an elastic member 102 is not limited to a leaf spring as illustrated in the figure, and may be made by an elastic material such as rubber. In addition, the elastic member 102 may be formed integrally with the cover member 100, which suppresses an increase in the number of components.

Effect of First Embodiment

According to the first embodiment described above, since the positioning member 14 is provided to protrude from the prism 12, the positioning member 14 is pressed by the inner wall of the cover member 100, and the prism 12 and the heat transfer member 13 are pressed toward the light transmission window 101 via the positioning member 14. As a result, the protruding end 13a of the heat transfer member 13 can abut with the light transmission window 101 even when attachment backlash between the prism 12 of the device main body 10 and the cover member 100 occurs as the space part is interposed between the prism 12 of the device main body 10 and the cover member 100.

Figure 7:
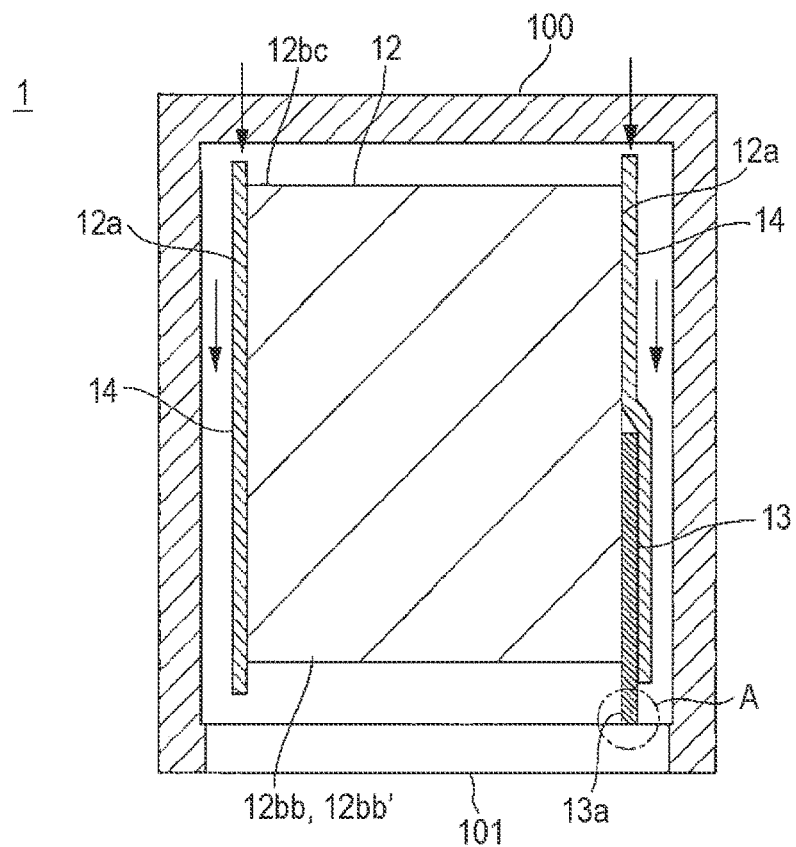
FIG. 7 is a cross-sectional view of a main part of the intraoral measurement device according to the first embodiment.

Here, FIG. 7 is a cross-sectional view of a main part of the intraoral measurement device 1 according to the first embodiment, and is a view corresponding to an A-A cross section of FIG. 6. As indicated by arrows in FIG. 7 and FIG. 6 above, when the protruding end 13a of the heat transfer member 13 is pressed toward the light transmission window 101 of the cover member 100 following the pressing of the positioning member 14, the protruding end 13a of the heat transfer member 13 easily abuts with the light transmission window 101 (see a part A in FIG. 7). As a result, condensation on the light transmission window 101 can be reliably inhibited.

Figure 8:
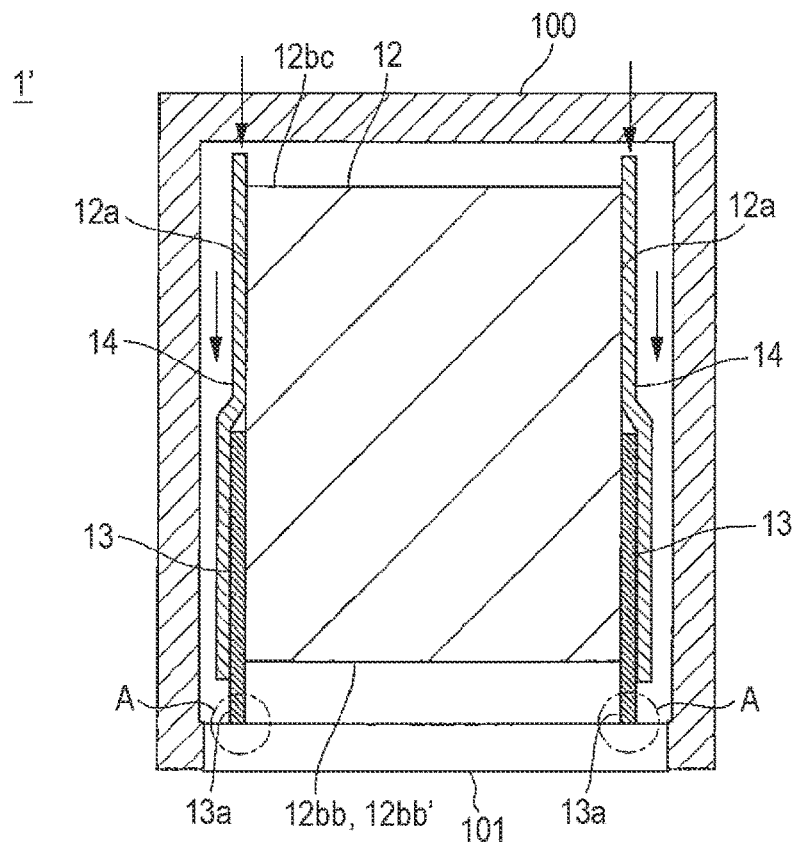
FIG. 8 is a cross-sectional view of a main part of an intraoral measurement device of a modification according to the first embodiment.

FIG. 8 is a cross-sectional view of a main part of an intraoral measurement device 1' of a modification according to the first embodiment, and is a view corresponding to the A-A cross section of FIG. 6. The modification illustrated in this figure is an example in which the heat transfer member 13 and the positioning member 14 are provided individually on the two non-optical surfaces 12a of the prism 12. Also in this case, similarly, the protruding end 13a of each heat transfer member 13 easily abuts with the light transmission window 101 (see a part A in FIG. 8). As a result, condensation on the light transmission window 101 can be more reliably inhibited by heating from the two heat transfer members 13.

Second Embodiment

Figure 9:
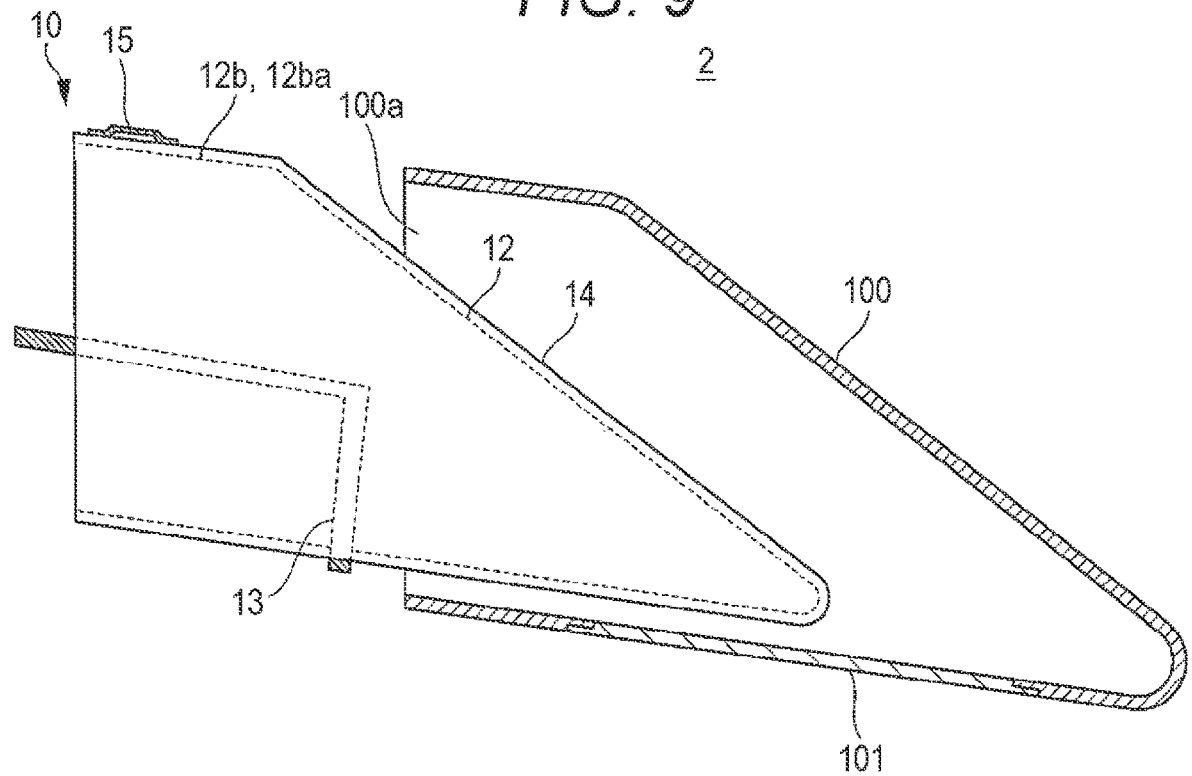
FIG. 9 is an enlarged view (part 1) of a main part for explaining a configuration of an intraoral measurement device according to a second embodiment.
Figure 10:
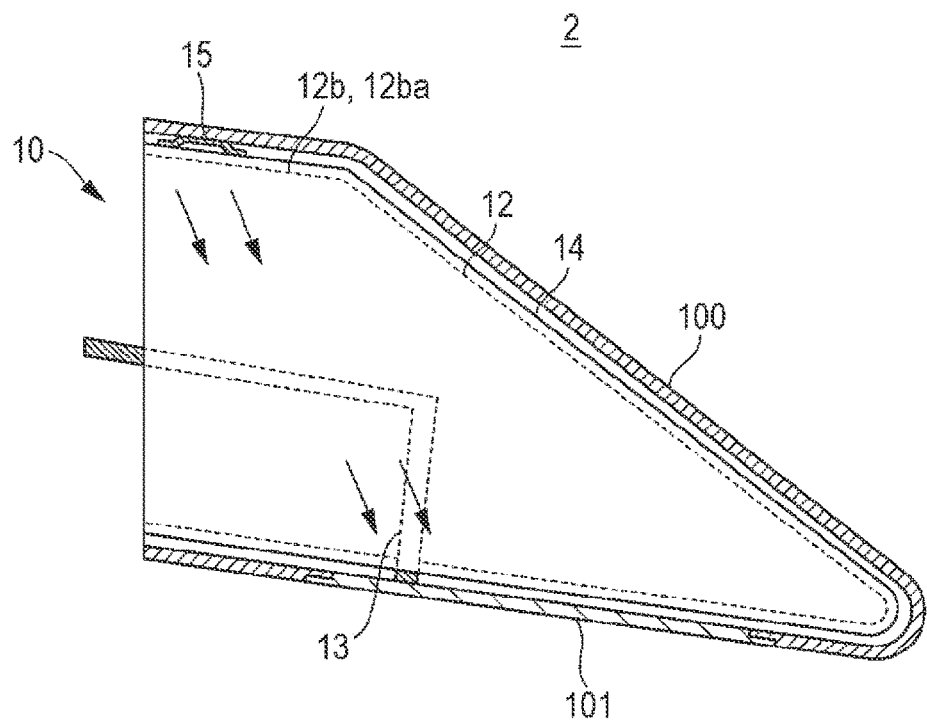
FIG. 10 is an enlarged view (part 2) of a main part for explaining the configuration of the intraoral measurement device according to the second embodiment.

FIGS. 9 and 10 are enlarged views (part 1) and (part 2) of a main part for explaining a configuration of an intraoral measurement device 2 according to a second embodiment. The intraoral measurement device 2 of the second embodiment illustrated in FIGS. 9 and 10 is different from the intraoral measurement device 1 of the first embodiment described with reference to FIGS. 1 to 8 in that an elastic member 15 is attached to a positioning member 14 on a device main body 10 side. Therefore, a cover member 100 is not provided with an elastic member. Other configurations are similar to those of the intraoral measurement device 1 of the first embodiment.

In this case, the elastic member 15 is provided at a position and with a size to press the positioning member 14 from a first surface 12ba side toward a second surface 12bb of a prism 12 via the cover member 100 in a state where the cover member 100 is attached to the device main body 10.

Such an elastic member 15 is provided, for example, at a peripheral edge of the positioning member 14 protruding from the first surface 12ba of the prism 12. Such an elastic member 15 is not limited to a leaf spring as illustrated in the figure, and may be made by an elastic material such as rubber. In addition, the elastic member 15 may be formed integrally with the positioning member 14, which suppresses an increase in the number of components.

Effect of Second Embodiment

Even in the intraoral measurement device 2 of the second embodiment described above, a protruding end 13a of a heat transfer member 13 is pressed toward a light transmission window 101 of the cover member 100 following the pressing of the positioning member 14 from the cover member 100 side. Therefore, effects similar to those of the first embodiment can be obtained.

Third Embodiment

Figure 11:
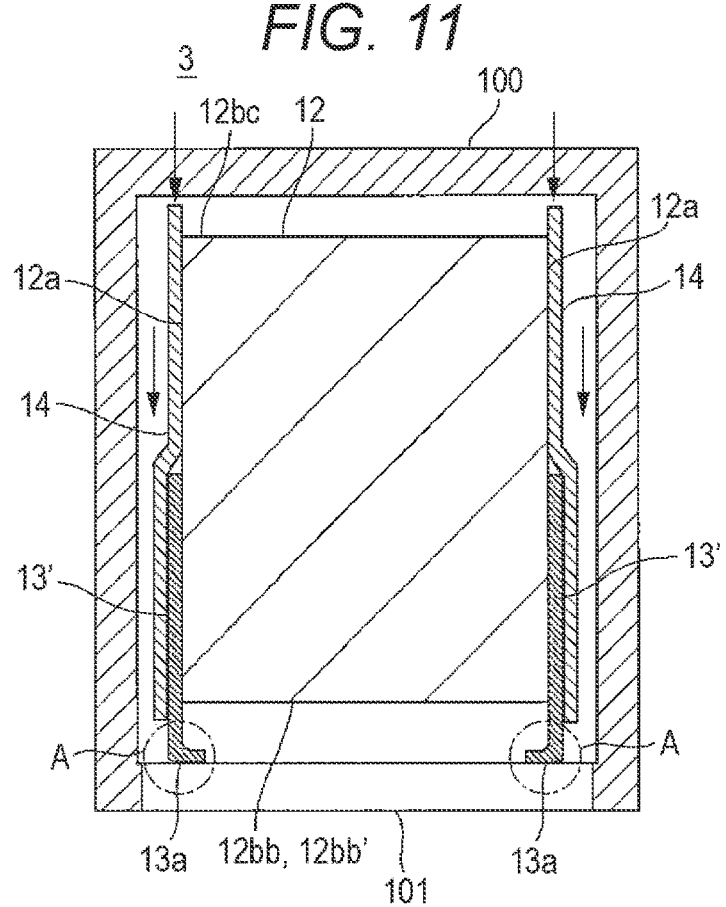
FIG. 11 is a cross-sectional view of a main part of an intraoral measurement device according to a third embodiment.

FIG. 11 is a cross-sectional view of a main part of an intraoral measurement device 3 according to a third embodiment, and is a view corresponding to the A-A cross section of FIG. 6. The intraoral measurement device 3 of the third embodiment illustrated in FIG. 11 is different from the intraoral measurement device 1 of the first embodiment described with reference to FIGS. 1 to 8 in a shape of a protruding end 13a' of a heat transfer member 13' provided along a non-optical surface 12a of a prism 12. Other configurations are similar to those of the intraoral measurement device 1 of the first embodiment.

In the heat transfer member 13', the protruding end 13a' protruding from the prism 12 is bent along an objective surface 12bb' of the prism 12 at a distal end of a protruding length [d] (see FIG. 3). That is, a distal end of the protruding end 13a' of the heat transfer member 13' is bent in parallel with a light transmission window 101 in a state where a cover member 100 is attached to a device main body 10.

A length of the distal end of the protruding end 13a', that is, a length from the bent part to the distal end side is made to be within a range in which transmission of measurement light is not affected in the objective surface 12bb'. In addition, a material of the bent part and the distal end side includes a material having a good thermal conductivity, such as silver, copper, gold, aluminum, nickel, or platinum similarly to a device main body portion of the heat transfer member 13', and may be the same material as or a different material from the device main body portion. However, the bent part of the heat transfer member 13' preferably has elasticity in consideration of mechanical strength, and is made by an elastic material or has a structure having elasticity by fine bending, for example. Further, the entire heat transfer member 13' may be integrally made by the same material. Moreover, it is also possible to adopt a structure reinforced by partially increasing a plate thickness of the bent part or supporting the bent part with a separate body.

Effect of Third Embodiment

According to the third embodiment described above, it is possible to increase a contact area between the protruding end 13a' of the heat transfer member 13' and the light transmission window 101, as compared with other embodiments. Therefore, heat-transfer effect from the protruding end 13a' to the light transmission window 101 is enhanced, and condensation on the light transmission window 101 can be more reliably inhibited.

Fourth Embodiment

Figure 12:
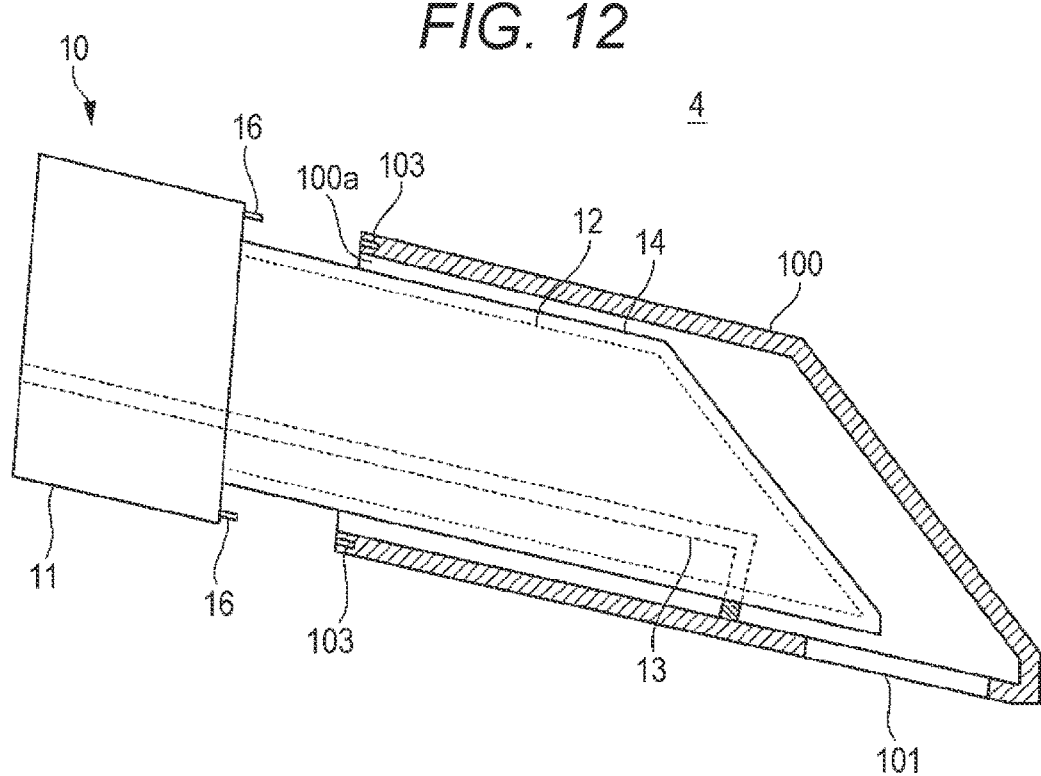
FIG. 12 is an enlarged view of a main part for explaining a configuration of an intraoral measurement device according to a fourth embodiment.

FIG. 12 is an enlarged view of a main part for explaining a configuration of an intraoral measurement device 4 according to a fourth embodiment. The intraoral measurement device 4 of the fourth embodiment illustrated in FIG. 12 is different from the intraoral measurement device 1 of the first embodiment described with reference to FIGS. 1 to 8 in that a positioning mechanism is provided in a housing 11 of a device main body 10 and a cover member 100, and other configurations are similar to those of the intraoral measurement device 1 of the first embodiment.

That is, in the housing 11 of the device main body 10, a positioning pin 16 as a fitting part is erected along an extending direction of a prism 12 at a position where a peripheral edge of an insertion port 100a of the cover member 100 abuts. Whereas, in the cover member 100, a positioning hole 103 into which the positioning pin 16 is inserted is provided as a fitting part, at a position where a peripheral edge of the housing 11 abuts in the device main body 10. The positioning pin 16 and the positioning hole 103 constitute a positioning mechanism between the device main body 10 and the cover member 100.

The positioning mechanism including the positioning pin 16 and the positioning hole 103 is preferably arranged at least at two positions. Further, the positioning pin 16 and the positioning hole 103 may be arranged reversely, in which the positioning pin may be provided in the cover member 100 and the positioning hole may be provided in the housing 11.

Effect of Fourth Embodiment

According to the fourth embodiment described above, since the positioning mechanism between the housing 11 and the cover member 100 is provided, an attachment state when the cover member 100 is attached to the device main body 10 can have a constant state. Therefore, even when a space part is interposed between the prism 12 of the device main body 10 and the cover member 100, attachment backlash between the prism 12 of the device main body 10 and the cover member 100 can be eliminated. This also ensures abutment between a protruding end 13a of a heat transfer member 13 and a light transmission window 101, which enables to reliably inhibit condensation on the light transmission window 101.

Fifth Embodiment

Figure 13:
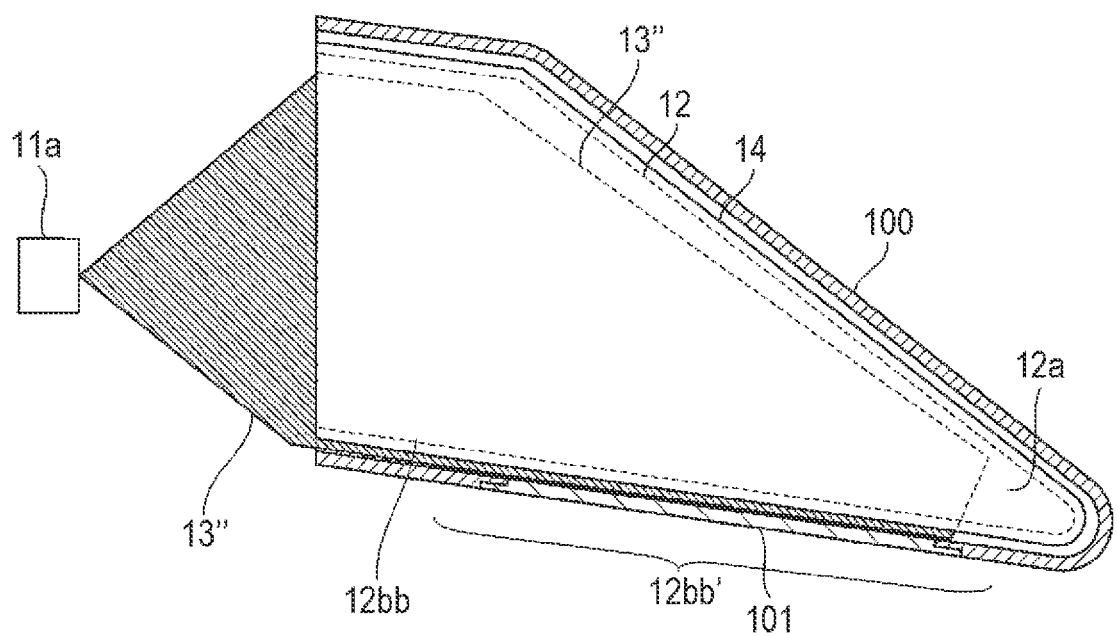
FIG. 13 is an enlarged view of a main part for explaining a configuration of an intraoral measurement device according to a fifth embodiment.

FIG. 13 is an enlarged view of a main part for explaining a configuration of an intraoral measurement device 5 according to a fifth embodiment. The intraoral measurement device 5 of the fifth embodiment illustrated in FIG. 13 is different from the intraoral measurement device 1 of the first embodiment described with reference to FIGS. 1 to 8 in a shape of a heat transfer member 13" provided along a non-optical surface 12a of a prism 12. Other configurations are similar to those of the intraoral measurement device 1 of the first embodiment.

That is, the heat transfer member 13" is not limited to a thin plate-shaped long member, and may have a thin plate shape with a wide shape along the non-optical surface 12a of the prism 12. In this case, as illustrated in FIG. 13, the heat transfer member 13" may be formed to have a large surface area from an illumination member 11a including a light source part serving as a heat source toward the non-optical surface 12a of the prism 12. Further, in a portion of the non-optical surface 12a of the prism 12, the heat transfer member 13" may have substantially the same surface shape as the non-optical surface 12a, and may protrude from the non-optical surface 12a within a range in which attachment of a cover member 100 is not affected.

In this case, a protruding end of the heat transfer member 13" is preferably provided to protrude from the non-optical surface 12a of the prism 12 with a similar width to a width of a light transmission window 101 of the cover member 100. Here, "similar width" includes the same width as the width of the light transmission window 101, means a width preferably 80% or more and more preferably 90% or more of the width of the light transmission window, and is more preferably larger than the width of the light transmission window 101 in consideration of a positional deviation. As a result, the protruding end 13a" protruding from the non-optical surface 12a in the heat transfer member 13" abuts with the light transmission window 101 of the cover member 100 in a wide range.

Effect of Fifth Embodiment

According to the fifth embodiment described above, since a surface area is formed to be wide from the illumination member toward the non-optical surface of the prism, heat generated in the illumination member can be effectively transferred to the light transmission window 101 by the heat transfer member 13". Such improvement in heat conduction efficiency makes it possible to reliably inhibit condensation on the light transmission window 101.

Note that the above-described embodiments and modifications can be combined, and the respective effects can be obtained by the combination.

Although embodiments of the present invention have been described and illustrated in detail, the disclosed embodiments are made for purposes of illustration and example only and not limitation. The scope of the present invention should be interpreted by terms of the appended claims.

What is claimed is:
1. An intraoral measurement device comprising:
a prism having a rectangular column shape and having a base end side and a distal end side, the distal end side facing a measurement target, the prism including:
a first optical surface;
a second optical surface opposite the first optical surface, the second optical surface having an objective surface that faces the measurement target;
a third optical surface inclined relative to the first optical surface; and
a first non-optical surface between the first optical surface and the second optical surface;
a device main body that holds the base end side of the prism by a housing, the housing accommodating an illumination member and an imaging member;
a cover member that is attached to the device main body in a state of covering, with a space part interposed in between, the distal end side of the prism, the cover member including a light transmission window that faces the measurement target;
a first heat transfer member that is fixed to the first non-optical surface of the prism, extends from the device main body along the first non-optical surface of the prism, has a protruding end that protrudes from the first non-optical surface of the prism to the light transmission window of the cover member, and transfers heat of the device main body to the light transmission window through abutment of the protruding end against the light transmission window of the cover member;
a first positioning member provided on the first non-optical surface of the prism, the first positioning member including a protruding portion that protrudes from the first non-optical surface in a direction opposite to the protruding end of the first heat transfer member is provided; and
a first elastic member between the protruding portion of the first positioning member and an inner wall of the cover member, wherein
the first positioning member presses the prism and the protruding end of the first heat transfer member toward the light transmission window, by being pressed toward the protruding end by the elastic member.
2. The intraoral measurement device according to claim 1, wherein
the cover member is freely attached to the device main body.
3. The intraoral measurement device according to claim 1, wherein
the first positioning member has a sheet shape in which a peripheral edge protrudes from the first non-optical surface of the prism, on the protruding end side of the first heat transfer member and an opposite side, and
the protruding end of the first heat transfer member protrudes larger than the first positioning member.
4. The intraoral measurement device according to claim 1, wherein the first elastic member is formed integrally with the cover member.
5. The intraoral measurement device according to claim 1, wherein
the first positioning member is provided with the first elastic member.

6. The intraoral measurement device according to claim 5, wherein
the first elastic member is formed integrally with the first positioning member.

7. The intraoral measurement device according to claim 1, further comprising a second heat transfer member, wherein
the prism has a second non-optical surface opposite the first non-optical surface, and
the second heat transfer member is fixed to the second non-optical surface of the prism, extends from the device main body along the second non-optical surface of the prism, has a protruding end that protrudes from the second non-optical surface of the prism to the light transmission window of the cover member, and transfers heat of the device main body to the light transmission window through abutment of the protruding end against the light transmission window of the cover member.

8. The intraoral measurement device according to claim 1, wherein
a distal end of the protruding end of the first heat transfer member is bent in parallel with the light transmission window of the cover member, in a state where the cover member is attached to the device main body.

9. The intraoral measurement device according to claim 8, wherein
a bent part of the protruding end of the heat transfer member has elasticity.

10. The intraoral measurement device according to claim 1, wherein
the device main body and the cover member have a plurality of fitting parts that are fitted to each other when the cover member is attached to the device main body.

11. The intraoral measurement device according to claim 1, wherein
the first heat transfer member transfers heat generated by the illumination member to the light transmission window.

12. The intraoral measurement device according to claim 11, wherein
the protruding end of the first heat transfer member is provided to protrude from the first non-optical surface of the prism, with a similar width to a width of the light transmission window of the cover member.

13. The intraoral measurement device according to claim 1, wherein
the first heat transfer member is fixed to the first non-optical surface of the prism by adhesion.

14. The intraoral measurement device according to claim 1, wherein
the first positioning member has a sheet shape covering the first non-optical surface of the prism, and is arranged to overlap with the first heat transfer member.

* * * * *